United States Patent
Albitov et al.

(10) Patent No.: US 12,127,757 B2
(45) Date of Patent: Oct. 29, 2024

(54) DEVICE FOR CONDITIONING EX VIVO PERICARDIAL TISSUE

(71) Applicant: CARDIOVALVE LTD., Or Yehuda (IL)

(72) Inventors: Michael Albitov, Kfar Saba (IL); Meni Iamberger, Kfar Saba (IL); Ilia Hariton, Zichron Yaakov (IL)

(73) Assignee: CARDIOVALVE LTD., Or Yehuda (IL)

(*) Notice: Subject to any disclaimer, the term of this patent is extended or adjusted under 35 U.S.C. 154(b) by 636 days.

(21) Appl. No.: 17/429,446

(22) PCT Filed: Dec. 23, 2019

(86) PCT No.: PCT/IL2019/051398
§ 371 (c)(1),
(2) Date: Aug. 9, 2021

(87) PCT Pub. No.: WO2020/165889
PCT Pub. Date: Aug. 20, 2020

(65) Prior Publication Data
US 2022/0133342 A1 May 5, 2022

(30) Foreign Application Priority Data
Feb. 11, 2019 (GB) ................................... 1901887

(51) Int. Cl.
*A61B 17/32* (2006.01)
(52) U.S. Cl.
CPC ........ *A61B 17/32* (2013.01); *A61B 2217/005* (2013.01); *A61B 2560/0214* (2013.01); *A61B 2560/0425* (2013.01)

(58) Field of Classification Search
CPC .............. A61B 17/32; A61B 2217/005; A61B 2560/0214; A61B 2560/0425
See application file for complete search history.

(56) References Cited

U.S. PATENT DOCUMENTS

| | | |
|---|---|---|
| 4,972,494 A | 11/1990 | White et al. |
| 5,201,757 A | 4/1993 | Heyn et al. |
| (Continued) | | |

FOREIGN PATENT DOCUMENTS

| | | |
|---|---|---|
| CN | 103974674 | 8/2014 |
| EP | 0170262 | 2/1986 |
| (Continued) | | |

OTHER PUBLICATIONS

An Office Action dated Sep. 9, 2021, which issued during the prosecution of U.S. Appl. No. 16/768,909.
(Continued)

*Primary Examiner* — Brooke Labranche
(74) *Attorney, Agent, or Firm* — Sughrue Mion, PLLC

(57) ABSTRACT

Embodiments of the present disclosure include a method for conditioning ex vivo pericardial tissue that has a parietal side and a fibrous side from which fibers extend. A blade assembly includes a blade head having a blade array and a face that defines gaps therein. The parietal side of the tissue is placed downward against a support plate, and a motor is operated to move the blade array with respect to the face. The face contacts the tissue such that the fibers protrude through the gaps and into the blade head. The blade array shears the fibers that protrude through the gaps into the blade head, yielding sheared fibers. Other embodiments are also described.

14 Claims, 6 Drawing Sheets

(56) References Cited

U.S. PATENT DOCUMENTS

| | | |
|---|---|---|
| 5,713,948 A | 2/1998 | Uflacker |
| 5,776,140 A | 7/1998 | Cottone |
| 5,957,949 A | 9/1999 | Leonhardt et al. |
| 5,961,549 A | 10/1999 | Nguyen et al. |
| 6,010,530 A | 1/2000 | Goicoechea |
| 6,245,105 B1 | 6/2001 | Nguyen et al. |
| 6,254,609 B1 | 7/2001 | Vrba et al. |
| 6,402,780 B2 | 6/2002 | Williamson, IV et al. |
| 6,413,275 B1 | 7/2002 | Nguyen et al. |
| 6,454,799 B1 | 9/2002 | Schreck |
| 6,733,525 B2 | 5/2004 | Yang et al. |
| 6,837,902 B2 | 1/2005 | Nguyen et al. |
| 7,018,406 B2 | 3/2006 | Seguin et al. |
| 7,074,236 B2 | 7/2006 | Rabkin et al. |
| 7,261,686 B2 | 8/2007 | Couvillon, Jr. |
| 7,585,321 B2 | 9/2009 | Cribier |
| 7,753,949 B2 | 7/2010 | Lamphere et al. |
| 7,811,296 B2 | 10/2010 | Goldfarb et al. |
| 8,070,802 B2 | 12/2011 | Lamphere et al. |
| 8,142,496 B2 | 3/2012 | Berreklouw |
| 8,361,144 B2 | 1/2013 | Fish et al. |
| 8,449,599 B2 | 5/2013 | Chau et al. |
| 8,568,475 B2 | 10/2013 | Nguyen et al. |
| 8,585,755 B2 | 11/2013 | Chau et al. |
| 8,628,571 B1 | 1/2014 | Hacohen et al. |
| 8,728,155 B2 | 5/2014 | Montorfano et al. |
| 8,850,898 B2 | 10/2014 | Johnsen |
| 8,852,272 B2 | 10/2014 | Gross et al. |
| 8,870,948 B1 | 10/2014 | Erzberger et al. |
| 8,870,950 B2 | 10/2014 | Hacohen |
| 8,945,177 B2 | 2/2015 | Dell et al. |
| 8,992,604 B2 | 3/2015 | Gross et al. |
| 8,998,982 B2 | 4/2015 | Richter et al. |
| 9,011,468 B2 | 4/2015 | Ketai et al. |
| 9,017,399 B2 | 4/2015 | Gross et al. |
| 9,023,100 B2 | 5/2015 | Quadri et al. |
| 9,095,434 B2 | 8/2015 | Rowe |
| 9,097,620 B2 | 8/2015 | Caron et al. |
| 9,119,719 B2 | 9/2015 | Zipory et al. |
| 9,132,009 B2 | 9/2015 | Hacohen et al. |
| 9,180,009 B2 | 11/2015 | Majkrzak et al. |
| 9,232,995 B2 | 1/2016 | Kovalsky et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,277,994 B2 | 3/2016 | Miller et al. |
| 9,295,551 B2 | 3/2016 | Straubinger et al. |
| 9,301,836 B2 | 4/2016 | Buchbinder et al. |
| 9,320,591 B2 | 4/2016 | Bolduc |
| 9,358,107 B2 | 6/2016 | Nguyen et al. |
| 9,387,078 B2 | 7/2016 | Gross et al. |
| 9,393,110 B2 | 7/2016 | Levi et al. |
| 9,439,757 B2 | 9/2016 | Wallace et al. |
| 9,492,273 B2 | 11/2016 | Wallace et al. |
| 9,532,870 B2 | 1/2017 | Cooper et al. |
| 9,554,899 B2 | 1/2017 | Granada et al. |
| 9,561,103 B2 | 2/2017 | Granada et al. |
| 9,597,182 B2 | 3/2017 | Straubinger et al. |
| 9,662,203 B2 | 5/2017 | Sheahan et al. |
| 9,681,952 B2 | 6/2017 | Hacohen et al. |
| 9,763,657 B2 | 9/2017 | Hacohen et al. |
| D800,908 S | 10/2017 | Hariton et al. |
| 9,788,941 B2 | 10/2017 | Hacohen |
| 9,895,226 B1 | 2/2018 | Harari et al. |
| 9,987,132 B1 | 6/2018 | Hariton et al. |
| 10,010,414 B2 | 7/2018 | Cooper et al. |
| 10,105,222 B1 | 10/2018 | Metchik et al. |
| 10,123,873 B1 | 11/2018 | Metchik et al. |
| 10,143,552 B2 | 12/2018 | Wallace et al. |
| 10,149,761 B2 | 12/2018 | Granada et al. |
| 10,154,903 B2 | 12/2018 | Albitov et al. |
| 10,154,906 B2 | 12/2018 | Granada et al. |
| 10,182,908 B2 | 1/2019 | Tubishevitz et al. |
| 10,226,341 B2 | 3/2019 | Gross et al. |
| 10,245,143 B2 | 4/2019 | Gross et al. |
| 10,258,471 B2 | 4/2019 | Lutter et al. |
| 10,292,816 B2 | 5/2019 | Raanani et al. |
| 10,299,927 B2 | 5/2019 | McLean et al. |
| 10,321,995 B1 | 6/2019 | Christianson et al. |
| 10,327,895 B2 | 6/2019 | Lozonschi et al. |
| 10,335,278 B2 | 7/2019 | McLean et al. |
| 10,376,361 B2 | 8/2019 | Gross et al. |
| 10,390,952 B2 | 8/2019 | Hariton et al. |
| 10,426,614 B2 | 10/2019 | Hariton et al. |
| 10,507,108 B2 | 12/2019 | Delgado et al. |
| 10,512,456 B2 | 12/2019 | Hacohen et al. |
| 10,517,719 B2 | 12/2019 | Miller et al. |
| 10,531,866 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,610,358 B2 | 4/2020 | Vidlund et al. |
| 10,631,871 B2 | 4/2020 | Goldfarb et al. |
| 10,667,912 B2 | 6/2020 | Dixon et al. |
| 10,702,385 B2 | 7/2020 | Hacohen et al. |
| 10,758,342 B2 | 9/2020 | Chau et al. |
| 10,779,946 B2 | 9/2020 | Kislev et al. |
| 10,842,627 B2 | 11/2020 | Delgado et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,874,514 B2 | 12/2020 | Dixon et al. |
| 10,888,422 B2 | 1/2021 | Hariton et al. |
| 10,888,425 B2 | 1/2021 | Delgado et al. |
| 10,888,644 B2 | 1/2021 | Ratz et al. |
| 10,905,548 B2 | 2/2021 | Hariton et al. |
| 10,905,552 B2 | 2/2021 | Dixon et al. |
| 10,905,554 B2 | 2/2021 | Cao |
| 10,918,483 B2 | 2/2021 | Metchik et al. |
| 10,925,732 B2 | 2/2021 | Delgado et al. |
| 10,945,843 B2 | 3/2021 | Delgado et al. |
| 10,945,844 B2 | 3/2021 | McCann et al. |
| 10,952,850 B2 | 3/2021 | Hariton et al. |
| 10,959,846 B2 | 3/2021 | Marr et al. |
| 10,993,809 B2 | 5/2021 | McCann et al. |
| 11,026,792 B2 | 6/2021 | Kislev et al. |
| 11,065,114 B2 | 7/2021 | Raanani et al. |
| 11,065,122 B2 | 7/2021 | Harari et al. |
| 11,083,582 B2 | 8/2021 | McCann et al. |
| 11,147,672 B2 | 10/2021 | McCann et al. |
| 11,179,240 B2 | 11/2021 | Delgado et al. |
| 11,291,545 B2 | 4/2022 | Hacohen |
| 11,291,546 B2 | 4/2022 | Gross et al. |
| 11,291,547 B2 | 4/2022 | Gross et al. |
| 11,291,844 B2 | 4/2022 | Gross |
| 11,304,805 B2 | 4/2022 | Hariton et al. |
| 11,304,806 B2 | 4/2022 | Hariton et al. |
| 11,389,297 B2 | 7/2022 | Franklin et al. |
| 11,426,155 B2 | 8/2022 | Hacohen et al. |
| 11,517,429 B2 | 12/2022 | Gross et al. |
| 11,517,436 B2 | 12/2022 | Hacohen |
| 2001/0005787 A1 | 6/2001 | Oz et al. |
| 2002/0032481 A1 | 3/2002 | Gabbay et al. |
| 2002/0151970 A1 | 10/2002 | Garrison et al. |
| 2003/0050694 A1 | 3/2003 | Yang et al. |
| 2003/0074059 A1 | 4/2003 | Nguyen et al. |
| 2004/0082991 A1 | 4/2004 | Nguyen et al. |
| 2004/0186558 A1 | 9/2004 | Pavcnik et al. |
| 2004/0249433 A1 | 12/2004 | Freitag |
| 2005/0080474 A1 | 4/2005 | Andreas et al. |
| 2005/0137688 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug et al. |
| 2005/0137699 A1 | 6/2005 | Salahieh et al. |
| 2005/0240200 A1 | 10/2005 | Bergheim |
| 2005/0251251 A1 | 11/2005 | Cribier |
| 2005/0256566 A1 | 11/2005 | Gabbay |
| 2006/0004469 A1 | 1/2006 | Sokel |
| 2006/0020275 A1 | 1/2006 | Goldfarb et al. |
| 2006/0020327 A1 | 1/2006 | Lashinski et al. |
| 2006/0052867 A1 | 3/2006 | Revuelta et al. |
| 2006/0122692 A1 | 6/2006 | Gilad et al. |
| 2006/0195183 A1 | 8/2006 | Navia et al. |

(56) References Cited

U.S. PATENT DOCUMENTS

| | | |
|---|---|---|
| 2006/0216404 A1 | 9/2006 | Seyler et al. |
| 2006/0259137 A1 | 11/2006 | Artof et al. |
| 2006/0282150 A1 | 12/2006 | Olson et al. |
| 2007/0016286 A1 | 1/2007 | Herrmann et al. |
| 2007/0056346 A1 | 3/2007 | Spenser et al. |
| 2007/0197858 A1 | 8/2007 | Goldfarb et al. |
| 2007/0198077 A1 | 8/2007 | Cully et al. |
| 2007/0213810 A1 | 9/2007 | Newhauser et al. |
| 2007/0213813 A1 | 9/2007 | Von Segesser et al. |
| 2007/0219630 A1 | 9/2007 | Chu |
| 2008/0065204 A1 | 3/2008 | Macoviak et al. |
| 2008/0071361 A1 | 3/2008 | Tuval et al. |
| 2008/0071369 A1 | 3/2008 | Tuval et al. |
| 2008/0147182 A1 | 6/2008 | Righini et al. |
| 2008/0200980 A1 | 8/2008 | Robin et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234813 A1 | 9/2008 | Heuser |
| 2008/0234814 A1 | 9/2008 | Salahieh et al. |
| 2008/0243245 A1 | 10/2008 | Thambar et al. |
| 2008/0281411 A1 | 11/2008 | Berreklouw |
| 2008/0294248 A1 | 11/2008 | Yang et al. |
| 2009/0005863 A1 | 1/2009 | Goetz et al. |
| 2009/0082844 A1 | 3/2009 | Zacharias et al. |
| 2009/0125098 A1 | 5/2009 | Chuter |
| 2009/0157175 A1 | 6/2009 | Benichou |
| 2009/0163934 A1 | 6/2009 | Raschdorf, Jr. et al. |
| 2009/0192601 A1 | 7/2009 | Rafiee et al. |
| 2009/0259306 A1 | 10/2009 | Rowe |
| 2010/0022823 A1 | 1/2010 | Goldfarb et al. |
| 2010/0023120 A1 | 1/2010 | Holecek et al. |
| 2010/0049306 A1 | 2/2010 | House et al. |
| 2010/0100167 A1 | 4/2010 | Bortlein et al. |
| 2010/0161036 A1 | 6/2010 | Pintor et al. |
| 2010/0185277 A1 | 7/2010 | Braido et al. |
| 2010/0312333 A1 | 12/2010 | Navia et al. |
| 2010/0324595 A1 | 12/2010 | Linder et al. |
| 2010/0331971 A1 | 12/2010 | Keränen et al. |
| 2011/0004299 A1 | 1/2011 | Navia et al. |
| 2011/0021985 A1 | 1/2011 | Spargias |
| 2011/0029072 A1 | 2/2011 | Gabbay |
| 2011/0082538 A1 | 4/2011 | Dahlgren et al. |
| 2011/0098802 A1 | 4/2011 | Braido et al. |
| 2011/0112632 A1 | 5/2011 | Chau et al. |
| 2011/0137397 A1 | 6/2011 | Chau et al. |
| 2011/0137410 A1 | 6/2011 | Hacohen |
| 2011/0144742 A1 | 6/2011 | Madrid et al. |
| 2011/0208283 A1 | 8/2011 | Rust |
| 2011/0208298 A1 | 8/2011 | Tuval et al. |
| 2011/0218620 A1 | 9/2011 | Meiri et al. |
| 2011/0224785 A1 | 9/2011 | Hacohen |
| 2011/0245911 A1 | 10/2011 | Quill et al. |
| 2011/0251683 A1 | 10/2011 | Tabor |
| 2011/0276128 A1 | 11/2011 | Cao et al. |
| 2011/0282439 A1 | 11/2011 | Thill et al. |
| 2011/0307049 A1 | 12/2011 | Kao |
| 2011/0319988 A1 | 12/2011 | Schankereli et al. |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0059458 A1 | 3/2012 | Buchbinder et al. |
| 2012/0065464 A1 | 3/2012 | Ellis et al. |
| 2012/0078237 A1 | 3/2012 | Wang et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0123530 A1 | 5/2012 | Carpentier et al. |
| 2012/0165930 A1 | 6/2012 | Gifford, III et al. |
| 2012/0300063 A1 | 11/2012 | Majkrzak et al. |
| 2012/0310328 A1 | 12/2012 | Olson et al. |
| 2013/0018458 A1 | 1/2013 | Yohanan et al. |
| 2013/0030519 A1 | 1/2013 | Tran et al. |
| 2013/0035759 A1 | 2/2013 | Gross et al. |
| 2013/0066341 A1 | 3/2013 | Ketai et al. |
| 2013/0066342 A1 | 3/2013 | Dell et al. |
| 2013/0150956 A1 | 6/2013 | Yohanan et al. |
| 2013/0178930 A1 | 7/2013 | Straubinger et al. |
| 2013/0253643 A1 | 9/2013 | Rolando et al. |
| 2013/0261738 A1 | 10/2013 | Clague et al. |
| 2013/0274870 A1 | 10/2013 | Lombardi et al. |
| 2013/0304200 A1 | 11/2013 | Mclean et al. |
| 2013/0331929 A1 | 12/2013 | Mitra et al. |
| 2014/0000112 A1 | 1/2014 | Braido et al. |
| 2014/0005767 A1 | 1/2014 | Glazier et al. |
| 2014/0005778 A1 | 1/2014 | Buchbinder et al. |
| 2014/0018915 A1 | 1/2014 | Biadillah et al. |
| 2014/0142688 A1 | 5/2014 | Duffy et al. |
| 2014/0172077 A1 | 6/2014 | Bruchman et al. |
| 2014/0207231 A1 | 7/2014 | Hacohen et al. |
| 2014/0214157 A1 | 7/2014 | Börtlein et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Börtlein et al. |
| 2014/0277411 A1 | 9/2014 | Börtlein et al. |
| 2014/0277412 A1 | 9/2014 | Börtlein et al. |
| 2014/0277418 A1 | 9/2014 | Miller |
| 2014/0324164 A1 | 10/2014 | Gross et al. |
| 2014/0331475 A1 | 11/2014 | Duffy et al. |
| 2014/0358222 A1 | 12/2014 | Gorman, III et al. |
| 2014/0358224 A1 | 12/2014 | Tegels et al. |
| 2015/0142100 A1 | 5/2015 | Morriss et al. |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0196390 A1 | 7/2015 | Ma et al. |
| 2015/0196393 A1 | 7/2015 | Vidlund et al. |
| 2015/0250588 A1 | 9/2015 | Yang et al. |
| 2015/0272730 A1 | 10/2015 | Melnick et al. |
| 2015/0272731 A1 | 10/2015 | Racchini et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0351903 A1 | 12/2015 | Morriss et al. |
| 2015/0351904 A1 | 12/2015 | Cooper et al. |
| 2016/0030169 A1 | 2/2016 | Shahriari |
| 2016/0030171 A1 | 2/2016 | Quijano et al. |
| 2016/0095700 A1 | 4/2016 | Righini |
| 2016/0220367 A1 | 8/2016 | Barrett |
| 2016/0310268 A1 | 10/2016 | Oba et al. |
| 2016/0317305 A1 | 11/2016 | Pelled et al. |
| 2016/0324635 A1 | 11/2016 | Vidlund et al. |
| 2016/0338706 A1 | 11/2016 | Rowe |
| 2016/0374801 A1 | 12/2016 | Jimenez et al. |
| 2016/0374802 A1 | 12/2016 | Levi et al. |
| 2017/0049435 A1 | 2/2017 | Sauer et al. |
| 2017/0056166 A1 | 3/2017 | Ratz et al. |
| 2017/0100236 A1 | 4/2017 | Robertson et al. |
| 2017/0135816 A1 | 5/2017 | Lashinski et al. |
| 2017/0165054 A1 | 6/2017 | Benson et al. |
| 2017/0189174 A1 | 7/2017 | Braido et al. |
| 2017/0224323 A1 | 8/2017 | Rowe et al. |
| 2017/0231757 A1 | 8/2017 | Gassler |
| 2017/0281337 A1 | 10/2017 | Campbell |
| 2017/0333187 A1 | 11/2017 | Hariton et al. |
| 2018/0000580 A1 | 1/2018 | Wallace et al. |
| 2018/0014930 A1 | 1/2018 | Hariton et al. |
| 2018/0021129 A1 | 1/2018 | Peterson et al. |
| 2018/0055629 A1 | 3/2018 | Oba et al. |
| 2018/0098850 A1 | 4/2018 | Rafiee et al. |
| 2018/0116790 A1 | 5/2018 | Ratz et al. |
| 2018/0116843 A1 | 5/2018 | Schreck et al. |
| 2018/0125644 A1 | 5/2018 | Conklin |
| 2018/0132999 A1 | 5/2018 | Perouse |
| 2018/0133003 A1 | 5/2018 | Levi |
| 2018/0153687 A1 | 6/2018 | Hariton et al. |

(56) References Cited

U.S. PATENT DOCUMENTS

| | | |
|---|---|---|
| 2018/0153695 A1 | 6/2018 | Cunningham et al. |
| 2018/0161159 A1 | 6/2018 | Lee et al. |
| 2018/0206982 A1 | 7/2018 | Haivatov et al. |
| 2018/0206983 A1 | 7/2018 | Noe et al. |
| 2018/0243086 A1 | 8/2018 | Barbarino et al. |
| 2018/0250126 A1 | 9/2018 | O'connor et al. |
| 2018/0250147 A1 | 9/2018 | Syed |
| 2018/0296333 A1 | 10/2018 | Dixon et al. |
| 2018/0296336 A1 | 10/2018 | Cooper et al. |
| 2018/0325671 A1 | 11/2018 | Abunassar et al. |
| 2018/0344457 A1 | 12/2018 | Gross et al. |
| 2018/0344490 A1 | 12/2018 | Fox et al. |
| 2018/0353294 A1 | 12/2018 | Calomeni et al. |
| 2019/0000613 A1 | 1/2019 | Delgado et al. |
| 2019/0015200 A1 | 1/2019 | Delgado et al. |
| 2019/0021852 A1 | 1/2019 | Delgado et al. |
| 2019/0038405 A1 | 2/2019 | Iamberger et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083261 A1 | 3/2019 | Perszyk et al. |
| 2019/0083262 A1 | 3/2019 | Hariton et al. |
| 2019/0105153 A1 | 4/2019 | Barash et al. |
| 2019/0117391 A1 | 4/2019 | Humair |
| 2019/0167423 A1 | 6/2019 | Hariton et al. |
| 2019/0175339 A1 | 6/2019 | Vidlund |
| 2019/0175342 A1 | 6/2019 | Hariton et al. |
| 2019/0183639 A1 | 6/2019 | Moore |
| 2019/0192295 A1 | 6/2019 | Spence et al. |
| 2019/0216602 A1 | 7/2019 | Lozonschi |
| 2019/0262507 A1 | 8/2019 | Adamek-bowers et al. |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0060818 A1 | 2/2020 | Geist et al. |
| 2020/0085578 A1 | 3/2020 | Kislev et al. |
| 2020/0281723 A1 | 9/2020 | Harari et al. |
| 2020/0405486 A1 | 12/2020 | Kislev et al. |
| 2021/0106419 A1 | 4/2021 | Abunassar |
| 2021/0113331 A1 | 4/2021 | Quadri et al. |
| 2021/0137680 A1 | 5/2021 | Kizuka et al. |
| 2021/0251759 A1 | 8/2021 | Kislev et al. |
| 2021/0259835 A1 | 8/2021 | Tyler, II et al. |
| 2022/0000612 A1 | 1/2022 | Hacohen |
| 2022/0023036 A1 | 1/2022 | Levi et al. |
| 2022/0061984 A1 | 3/2022 | Humair et al. |
| 2022/0105238 A1 | 4/2022 | Reimer et al. |
| 2022/0151779 A1 | 5/2022 | Pintor |

FOREIGN PATENT DOCUMENTS

| | | |
|---|---|---|
| EP | 1264582 | 12/2002 |
| EP | 1637092 | 3/2006 |
| EP | 2641569 | 9/2013 |
| EP | 2349124 | 10/2018 |
| EP | 3583922 | 12/2019 |
| EP | 3270825 | 4/2020 |
| EP | 2485795 | 9/2020 |
| GB | 844190 | 8/1960 |
| JP | S53152790 | 12/1978 |
| KR | 20010046894 | 6/2001 |
| WO | 1998/043557 | 10/1998 |
| WO | 01/82832 | 11/2001 |
| WO | 2004/028399 | 4/2004 |
| WO | 2006/007389 | 1/2006 |
| WO | 2006/113906 | 10/2006 |
| WO | 2006/128193 | 11/2006 |
| WO | 2007/047488 | 4/2007 |
| WO | 2010/006627 | 1/2010 |
| WO | 2010/027485 | 3/2010 |
| WO | 2010/057262 | 5/2010 |
| WO | 2011/057087 | 5/2011 |
| WO | 2011/072084 | 6/2011 |
| WO | 2011/144351 | 11/2011 |
| WO | 2012/011108 | 1/2012 |
| WO | 2012/048035 | 4/2012 |
| WO | 2012/177942 | 12/2012 |
| WO | 2012/178115 | 12/2012 |
| WO | 2013/021374 | 2/2013 |
| WO | 2013/021375 | 2/2013 |
| WO | 2013/028387 | 2/2013 |
| WO | 2013/059743 | 4/2013 |
| WO | 2013/059747 | 4/2013 |
| WO | 2013/072496 | 5/2013 |
| WO | 2013/078497 | 6/2013 |
| WO | 2013/114214 | 8/2013 |
| WO | 2013/175468 | 11/2013 |
| WO | 2014/076696 | 5/2014 |
| WO | 2014/115149 | 7/2014 |
| WO | 2014/121275 | 8/2014 |
| WO | 2014/121280 A2 | 8/2014 |
| WO | 2014/144937 | 9/2014 |
| WO | 2014/164364 | 10/2014 |
| WO | 2016/016899 | 2/2016 |
| WO | 2016/125160 | 8/2016 |
| WO | 2016/183526 | 11/2016 |
| WO | 2018/025263 | 2/2018 |
| WO | 2018/029680 | 2/2018 |
| WO | 2018/039631 | 3/2018 |
| WO | 2019/026059 | 2/2019 |
| WO | 2019/027507 | 2/2019 |
| WO | 2019/030753 | 2/2019 |
| WO | 2019/077595 | 4/2019 |
| WO | 2019/086958 | 5/2019 |
| WO | 2019/116369 | 6/2019 |
| WO | 2019/138400 | 7/2019 |
| WO | 2019/195860 | 10/2019 |
| WO | 2019/202579 | 10/2019 |
| WO | 2020/058972 | 3/2020 |
| WO | 2020/165889 | 8/2020 |
| WO | 2021/156866 A1 | 8/2021 |
| WO | 2021/186424 | 9/2021 |
| WO | 2022/046568 | 3/2022 |
| WO | 2022/061017 | 3/2022 |

OTHER PUBLICATIONS

An Office Action dated Sep. 15, 2021, which issued during the prosecution of U.S. Appl. No. 16/135,599.

An Office Action dated Oct. 14. 2021, which issued during the prosecution of U.S. Appl. No. 16/680,739.

An Office Action dated Oct. 21, 2021, which issued during the prosecution of U.S. Appl. No. 17/335,845.

European Search Report dated Oct. 11, 2021 which issued during the prosecution of Applicant's European App No. 21176010.3.

Fann, James I., et al. "Beating heart catheter-based edge-to-edge mitral valve procedure in a porcine model: efficacy and healing response." Circulation 110.8 (2004): 988-993.

Feldman, Ted, et al. "Percutaneous mitral repair with the MitraClip system: safety and midterm durability in the initial EVEREST (Endovascular Valve Edge-to-Edge REpair Study) cohort." Journal of the American College of Cardiology 54.8 (2009): 686-694.

IPR2021-00383 Patent Owner's Contingent Motion To Amend Under 37 C.F.R. §42.121 dated Oct. 13, 2021.

IPR2021-00383 Patent Owner's Response Pursuant to 37 C.F.R. § 42.120 dated Oct. 13, 2021.

IPR2021-00383 Second Declaration of Dr. Michael Sacks dated Oct. 13, 2021.

An Office Action dated Oct. 21, 2021, which issued during the prosecution of U.S. Appl. No. 17/306,231.

Maisano, Francesco, et al. "The evolution from surgery to percutaneous mitral valve interventions: the role of the edge-to-edge technique." Journal of the American College of Cardiology 58.21 (2011): 2174-2182.

IPR2021-00383 Deposition of Dr. Ivan Vesely, dated Sep. 22, 2021.

(56) References Cited

OTHER PUBLICATIONS

Cardiovalve Exhibit 2009—Percutaneous Mitral Leaflet Repair: MitraClip® Therapy for Mitral Regurgitation (2012).
Feldman, Ted, et al. "Percutaneous mitral valve repair using the edge-to-edge technique: six-month results of the EVEREST Phase I Clinical Trial." Journal of the American College of Cardiology 46.11 (2005): 2134-2140.
An Office Action summarized English translation and Search Report dated Oct. 8, 2021, which issued during the prosecution of Chinese Patent Application No. 201780061210.3.
An Office Action dated Nov. 4, 2021, which issued during the prosecution of U.S. Appl. No. 17/366,711.
An Office Action summarized English translation and Search Report dated Aug. 12, 2021, which issued during the prosecution of Chinese Patent Application No. 201880058940.2.
Maisano, F., et al. "The edge-to-edge technique: a simplified method to correct mitral insufficiency." European journal of cardio-thoracic surgery 13.3 (1998): 240-246.
Fucci, C., et al. "Improved results with mitral valve repair using new surgical techniques." European journal of cardio-thoracic surgery 9.11 (1995): 621-627.
An Office Action dated Jul. 27, 2022, which issued during the prosecution of U.S. Appl. No. 16/881,350.
An Office Action dated Sep. 21, 2022, which issued during the prosecution of U.S. Appl. No. 16/776,581.
An Office Action dated Jul. 20, 2022, which issued during the prosecution of U.S. Appl. No. 17/101,787.
An Office Action dated Sep. 16, 2022, which issued during the prosecution of U.S. Appl. No. 16/135,466.
An Office Action dated Aug. 1, 2022, which issued during the prosecution of European Patent Application No. 18826823.9.
European Search Report dated Sep. 6, 2022 which issued during the prosecution of Applicant's European App No. 22161862.2.
IPR2021-01051 Petitioners' Reply to Preliminary Guidance dated Aug. 2, 2022.
IPR2021-01051 Patent Owner's Sur-Reply to Petitioners' Reply to Preliminary Guidance dated Aug. 23, 2022.
An Office Action dated Aug. 5, 2022, which issued during the prosecution of U.S. Appl. No. 16/760,147.
An Office Action dated Sep. 8, 2022, which issued during the prosecution of U.S. Appl. No. 16/896,858.
An Office Action dated Sep. 29, 2022, which issued during the prosecution of U.S. Appl. No. 17/010,886.
An Office Action dated Sep. 29, 2022, which issued during the prosecution of U.S. Appl. No. 16/656,790.
Notice of Allowance dated Sep. 20, 2023, which issued during the prosecution of U.S. Appl. No. 17/839,538.
An Office Action dated Oct. 13, 2023, which issued during the prosecution of U.S. Appl. No. 17/181,722.
Grounds of Opposition to European Patent No. EP 2 948 103, filed Sep. 6, 2023.
An Office Action dated Aug. 31, 2023, which issued during the prosecution of U.S. Appl. No. 17/397,235.
An Office Action dated Sep. 8, 2023, which issued during the prosecution of U.S. Appl. No. 18/216,391.
An Office Action dated Sep. 8, 2023, which issued during the prosecution of U.S. Appl. No. 18/218,419.
Opposition to European Patent No. EP 2 948 103, filed Sep. 6, 2023.
An International Search Report and a Written Opinion both dated Aug. 23, 2023, 2023, which issued during the prosecution of Applicant's PCT/IL2023/050586.
An Office Action dated Aug. 3, 2023, which issued during the prosecution of U.S. Appl. No. 17/683,875.
An International Search Report and a Written Opinion both dated Sep. 13, 2023, which issued during the prosecution of Applicant's PCT/IL2023/050587.
An Office Action dated Feb. 28, 2024, which issued during the prosecution of Canadian Patent Application No. 3,129,355.
An Office Action dated Jan. 26, 2022, which issued during the prosecution of U.S. Appl. No. 16/888,210.
Notice of Allowance dated Jan. 31, 2022, which issued during the prosecution of U.S. Appl. No. 17/479,418.
An Office Action dated Mar. 18, 2022, which issued during the prosecution of U.S. Appl. No. 16/746,489.
Notice of Allowance dated Mar. 22, 2022, which issued during the prosecution of U.S. Appl. No. 17/366,711.
Notice of Allowance dated Mar. 4, 2022, which issued during the prosecution of U.S. Appl. No. 16/768,909.
An Office Action dated Dec. 9, 2021, which issued during the prosecution of U.S. Appl. No. 16/135,969.
An Office Action dated Jan. 24, 2022, which issued during the prosecution of U.S. Appl. No. 16/135,466.
An Office Action dated Apr. 11, 2022, which issued during the prosecution of U.S. Appl. No. 17/473,472.
IPR2021-00383 Preliminary Guidance dated Jan. 31, 2022.
An International Search Report and a Written Opinion both dated May 3, 2022, which issued during the prosecution of Applicant's PCT/IL2021/051433.
An Office Action dated Jul. 8, 2022, which issued during the prosecution of U.S. Appl. No. 16/144,054.
An Office Action dated Jun. 28, 2022, which issued during the prosecution of U.S. Appl. No. 16/135,969.
An Office Action together with an English Summary dated May 7, 2022 which issued during the prosecution of Chinese Patent Application No. 201880058940.2.
Ex Parte Quayle dated May 2, 2022, which issued during the prosecution of U.S. Appl. No. 16/879,952.
IPR2021-00383 Final Written Decision dated Jul. 18, 2022.
IPR2021-01051 Preliminary Guidance Patent Owner's Motion to Amend dated Jun. 24, 2022.
Notice of Allowance dated May 4, 2022, which issued during the prosecution of U.S. Appl. No. 16/680,739.
An Office Action dated Nov. 25, 2021, which issued during the prosecution of European Patent Application No. 18826823.9.
IPR2021-01051 Institution decision dated Dec. 10, 2021.
Notice of Allowance dated Dec. 7, 2021, which issued during the prosecution of U.S. Appl. No. 17/394,807.
Notice of Allowance dated Dec. 6, 2021, which issued during the prosecution of U.S. Appl. No. 16/738,516.
Notice of Allowance dated Dec. 29, 2021, which issued during the prosecution of U.S. Appl. No. 17/210,183.
IPR2021-00383 Petitioners' Reply to Patent Owner's Response dated Jan. 5, 2022.
IPR2021-00383 Petitioners' Opposition to Patent Owner's Contingent Motion to Amend dated Jan. 5, 2022.
An Office Action dated Sep. 22, 2021, which issued during the prosecution of European Patent Application No. 20714289.4.
Summary of Examination Notice dated Jan. 6, 2022, which issued during the prosecution of Chinese Patent Application No. 201880064313.X.
An Office Action dated Jan. 12, 2022, which issued during the prosecution of U.S. Appl. No. 17/101,787.
Notice of Allowance dated Dec. 22, 2017, which issued during the prosecution of U.S. Appl. No. 15/788,407.
An International Search Report and a Written Opinion both dated Jun. 20, 2018, which issued during the prosecution of Applicant's PCT/IL2018/050024.
An International Preliminary Report on Patentability dated Apr. 21, 2020, which issued during the prosecution of Applicant's PCT/IL2018/050024.
An International Search Report and a Written Opinion both dated Nov. 9, 2018, which issued during the prosecution of Applicant's PCT/IL2018/050869.
An International Search Report and a Written Opinion both dated May 13, 2019, which issued during the prosecution of Applicant's PCT/IL2018/051350.
An International Search Report and a Written Opinion both dated Apr. 25, 2019, which issued during the prosecution of Applicant's PCT/IL2019/050142.
An International Search Report and a Written Opinion both dated Jan. 25, 2019, which issued during the prosecution of Applicant's PCT/IL2018/051122.

(56) References Cited

OTHER PUBLICATIONS

An International Search Report and a Written Opinion both dated Dec. 5, 2018, which issued during the prosecution of Applicant's PCT/IL2018/050725.
An International Preliminary Report on Patentability dated Feb. 12. 2019, which issued during the prosecution of Applicant's PCT/IL2017/050873.
An International Preliminary Report on Patentability dated Feb. 5, 2019, which issued during the prosecution of Applicant's PCT/IL2017/050849.
An Office Action dated Mar. 25, 2019, which issued during the prosecution of European Patent Application No. 14710060.6.
An Office Action dated Oct. 25, 2018, which issued during the prosecution of U.S. Appl. No. 14/763,004.
An Office Action dated Mar. 4, 2019, which issued during the prosecution of U.S. Appl. No. 14/763,004.
An Office Action dated Jan. 9, 2019, which issued during the prosecution of U.S. Appl. No. 15/329,920.
An Office Action dated Jan. 30, 2019, which issued during the prosecution of U.S. Appl. No. 15/872,501.
An Office Action dated May 14, 2020, which issued during the prosecution of U.S. Appl. No. 16/132,937.
An Office Action dated Feb. 5, 2019, which issued during the prosecution of U.S. Appl. No. 15/899,858.
An Office Action dated May 23, 2019, which issued during the prosecution of U.S. Appl. No. 15/668,659.
An Office Action dated May 1, 2019, which issued during the prosecution of U.S. Appl. No. 15/691,032.
An Office Action dated May 16, 2019, which issued during the prosecution of U.S. Appl. No. 15/433,547.
An Office Action dated Aug. 1, 2019, which issued during the prosecution of U.S. Appl. No. 15/668,559.
An Office Action dated Jun. 25, 2019, which issued during the prosecution of U.S. Appl. No. 15/329,920.
An Office Action dated Nov. 1, 2019, which issued during the prosecution of U.S. Appl. No. 15/872,501.
An Office Action dated Aug. 16, 2019, which issued during the prosecution of U.S. Appl. No. 15/668,659.
An Office Action dated Jun. 19, 2019, which issued during the prosecution of U.S. Appl. No. 15/682,789.
An Office Action dated Jun. 14, 2019, which issued during the prosecution of U.S. Appl. No. 15/703,385.
An Office Action dated Oct. 4, 2019, which issued during the prosecution of U.S. Appl. No. 16/183,140.
An Office Action dated Sep. 13, 2019, which issued during the prosecution of U.S. Appl. No. 16/460,313.
An Office Action dated Nov. 26, 2019, which issued during the prosecution of U.S. Appl. No. 16/532,945.
An Office Action dated Jun. 13. 2019, which issued during the prosecution of U.S. Appl. No. 16/388,038.
An Office Action dated Jan. 6, 2020, which issued during the prosecution of U.S. Appl. No. 16/660,231.
Notice of Allowance dated Oct. 19, 2020, which issued during the prosecution of U.S. Appl. No. 16/937,216.
An Office Action dated Aug. 13, 2019, which issued during the prosecution of UK Patent Application No. 1901887.8.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
Notice of Allowance dated Jan. 13, 2020, which issued during the prosecution of U.S. Appl. No. 15/956,956.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
An Office Action dated Sep. 24, 2020, which issued during the prosecution of U.S. Appl. No. 16/811,732.
Symetis S.A.: "Acurate neo™ Aortic Bioprosthesis for Implantation using the Acurate neo™ TA Transapical Delivery System in Patients with Severe Aortic Stenosis," Clinical Investigation Plan, Protocol No. 2015-01, Version # 2 (2015): 1-76.
An Office Action dated Nov. 30, 2020, which issued during the prosecution of U.S. Appl. No. 16/138,129.
Notice of Allowance dated Nov. 19, 2020, which issued during the prosecution of U.S. Appl. No. 16/318,025.
An Office Action dated Oct. 5, 2020, which issued during the prosecution of Canadian Patent Application No. 2,973,940.
An International Preliminary Report on Patentability dated Oct. 20, 2020, which issued during the prosecution of Applicant's PCT/IL2019/050142.
An Office Action summarized English translation and Search Report dated Nov. 25. 2020, which issued during the prosecution of Chinese Patent Application No. 201910449820.1.
An International Search Report and a Written Opinion both dated Jan. 28, 2020, which issued during the prosecution of Applicant's PCT/IL2019/051031.
European Search Report dated May 7, 2021 which issued during the prosecution of Applicant's European App No. 18700954.3.
Sündermann, Simon H., et al. "Feasibility of the Engager™ aortic transcatheter valve system using a flexible over-the-wire design." European Journal of Cardio-Thoracic Surgery 42.4 (2012): e48-e52.
Serruys, P. W., Piazza, N., Cribier, A., Webb, J., Laborde, J. C., & de Jaegere, P. (Eds.). (2009). Transcatheter aortic valve implantation: tips and tricks to avoid failure. CRC Press.—Screenshots from Google Books downloaded from: https://books.google.co.il/books?id=ELzLBQAAQBAJ&lpg=PA198&ots=soqWrDH-y_&dq=%20%22Edwards%20SAPIEN%22&lr&pg=PA20#v=onepage&q=%22Edwards%20SAPIEN%22&f=false ; Downloaded on Jun. 18, 2020.
Notice of Allowance dated May 7, 2020, which issued during the prosecution of U.S. Appl. No. 16/637,166.
An Office Action dated Aug. 7, 2020, which issued during the prosecution of U.S. Appl. No. 15/668,659.
Notice of Allowance dated Jul. 29, 2020, which issued during the prosecution of U.S. Appl. No. 16/132,937.
Notice of Allowance dated Sep. 10, 2020, which issued during the prosecution of U.S. Appl. No. 15/600,190.
An Office Action dated Jul. 29, 2020, which issued during the prosecution of U.S. Appl. No. 16/269,328.
Notice of Allowance dated Aug. 26, 2020, which issued during the prosecution of U.S. Appl. No. 16/269,328.
An Office Action dated Jul. 14, 2020, which issued during the prosecution of U.S. Appl. No. 16/324,339.
Notice of Allowance dated Aug. 28, 2020, which issued during the prosecution of U.S. Appl. No. 16/324,339.
An Office Action summarized English translation and Search Report dated Jul. 3, 2020, which issued during the prosecution of Chinese Patent Application No. 201780061210.3.
Tchetche, D. and Nicolas M. Van Mieghem: "New-generation TAVI devices: description and specifications" EuroIntervention, 2014, No. 10:U90-U100.
An International Search Report and a Written Opinion both dated Jun. 24, 2020, which issued during the prosecution of Applicant's PCT/IL2019/051398.
Notice of Allowance dated Feb. 9, 2021, which issued during the prosecution of U.S. Appl. No. 16/937,216.
Notice of Allowance dated Dec. 23, 2020, which issued during the prosecution of U.S. Appl. No. 16/937,216.
Notice of Allowance dated Mar. 31, 2021, which issued during the prosecution of U.S. Appl. No. 16/756,235.
Notice of Allowance dated Mar. 22, 2021, which issued during the prosecution of U.S. Appl. No. 16/756,235.

(56) References Cited

OTHER PUBLICATIONS

An International Search Report and a Written Opinion both dated Feb. 23, 2021, which issued during the prosecution of Applicant's PCT/IL2020/050315.
An International Preliminary Report on Patentability dated Mar. 9, 2021, which issued during the prosecution of Applicant's PCT/IL2019/051031.
European Search Report dated Jun. 10, 2021 which issued during the prosecution of Applicant's European App No. 21157988.3.
An Invitation to pay additional fees dated May 19, 2021, which issued during the prosecution of Applicant's PCT/IL2021/050132.
An International Search Report and a Written Opinion both dated Jul. 12, 2021, which issued during the prosecution of Applicant's PCT/IL2021/050132.
IPR2021-00383 Petitioners' Authorized Reply to Patent Owner's Preliminary Response dated May 27, 2021.
Exhibit 1014—Transcript of proceedings held May 20, 2021 (*Edwards Lifesciences* vs. *Cardiovalve*).
Exhibit 1015—Facilitate, Meriam-Webster.com, https://www.merriamwebster.com/dictionary/facilitate (visited May 26, 2021).
Patent Owner's Authorized Surreply to Petitioner's Reply to Patent Owner's Preliminary Response dated Jun. 4, 2021(*Edwards Lifesciences* vs. *Cardiovalve*).
An Office Action dated Aug. 18, 2021, which issued during the prosecution of U.S. Appl. No. 17/210,183.
Institution decision dated Jul. 20, 2021(*Edwards Lifesciences* vs. *Cardiovalve*).
An International Preliminary Report on Patentability dated Aug. 10, 2021, which issued during the prosecution of Applicant's PCT/IL2019/051398.
Petition for Inter Partes Review of U.S. Pat. No. 10,702,385—dated Jun. 4, 2021.
Declaration of Ivan Vesely, Ph.D. in Support of Petition for Inter Partes Review of U.S. Pat. No. 10,702,385—dated Jun. 4, 2021.
Declaration of Dr. Ivan Vesely, Ph.D. in Support of Petition for Inter Partes Review of U.S. Pat. No. 10,226,341—dated Dec. 17, 2020.
Petition for Inter Partes Review of U.S. Pat. No. 10,226,341 and Exhibits 1001-1013—dated Dec. 29, 2020.
English Translation of Office Action dated May 14, 2024, which issued during the prosecution of Chinese Patent Application No. 201980095188.3.

DEVICE FOR CONDITIONING EX VIVO PERICARDIAL TISSUE

CROSS-REFERENCES TO RELATED APPLICATIONS

The present application is the US national phase of PCT application IL2019/051398, which published as WO 2020/165889, and which claims priority from UK patent application 1901887.8 (now terminated before grant) to Albitov et al., filed Feb. 11, 2019, which is assigned to the assignee of the present application, and which is incorporated herein by reference.

FIELD OF THE INVENTION

Some applications of the present invention relate in general to techniques for conditioning ex vivo fibrous tissue. More specifically, some applications of the present invention relate to techniques for removing fibers from ex vivo pericardial tissue in order to prepare the tissue for subsequent incorporation, as a prosthetic leaflet, into a prosthetic heart valve.

BACKGROUND

Xenographic use of pericardial tissue from animal sources is common practice in implantation of prosthetic heart valves to human patients. Particularly, ex vivo pericardial tissue is often used as raw material for preparation of prosthetic heart valve leaflets.

SUMMARY OF THE INVENTION

The present invention is directed to apparatus and methods for conditioning ex vivo pericardial tissue, in particular, this conditioning can include removing fibers that extend from a fibrous side of the tissue.

Aspects of the present invention include apparatus and methods for removing fibers from ex vivo pericardial tissue using a blade assembly comprising a motor configured to receive electrical power and to power a drive shaft. The drive shaft operatively connects the motor to a blade head. The blade head comprises a blade array operatively connected to the drive shall to move the blade array. The blade head comprises a face defining gaps dimensioned to facilitate protrusion therethrough of the fibers into the blade head. Applying the electrically powered blade assembly to a surface of the tissue removes fibers from the tissue by moving the blade array, with respect to the face, shearing the fibers that protrude through the gaps into the blade head.

Some aspects of the present invention include a separate battery pack configured to transmit electrical power to the motor.

Some aspects of the present invention include a separate controller configured to control the motor by controlling transmission of electrical power to the motor.

Some aspects of the present invention include apparatus and methods for removing fibers from ex vivo pericardial tissue while the tissue is submerged in a liquid within a bath, with the fibers facing upward, with the blade head facing downward, and with the blade array submerged in the liquid. The blade-assembly housing is typically shaped to define an exhaust hole. While the blade array is submerged in the liquid, the liquid is sucked into the blade head, and discharges a refuse liquid through the exhaust hole. For some applications, this suction is provided by movement of the blade array by the motor. For some applications, a distinct pump is configured to discard the liquid via a refuse hose, and to supply fresh liquid to the tissue via an inlet hose.

There is therefore provided, in accordance with an application of the present invention, apparatus for conditioning ex vivo pericardial tissue, the tissue having a parietal side, and a fibrous side from which fibers extend, the apparatus including:
   a blade assembly including:
      a blade head that includes:
         a blade array; and
         a face, the face defining gaps therein, the gaps dimensioned to facilitate protrusion therethrough of the fibers into the blade head, such that movement of the blade array, with respect to the face, shears the fibers that protrude through the gaps into the blade head:
      a motor;
      a drive shaft, the drive shaft operatively connecting the motor to the blade array; and
      a blade-assembly housing that houses the blade head, the motor, and the drive shaft;
   and:
      the blade assembly is configured to be used while the tissue is submerged in a liquid with the fibers facing upward, with the face facing downward, and with the blade array submerged in the liquid;
      the blade-assembly housing is shaped to define an exhaust hole; and
      the apparatus is configured to generate, while the blade array is submerged in the liquid, a suction force that sucks the liquid into the blade head via the gaps, and discharges a refuse liquid through the exhaust hole.

In an application, the apparatus includes a refuse hose connected to the exhaust hole, and leading away from the blade assembly.

In an application, the apparatus is configured such that movement of the blade array with respect to the face generates the suction force.

In an application, the apparatus is configured such that rotation of the blade array with respect to the face generates the suction force.

In an application, the apparatus includes a pump, the pump being:
   fluidly connected to the exhaust hole; and
   configured to generate the suction force.

In an application, the apparatus includes a refuse hose connected to the exhaust hole, and the pump is fluidly connected to the exhaust hole via the refuse hose.

In an application, the apparatus includes an inlet hose, the inlet hose configured to be connected to a source of fresh liquid, and the pump is:
   connected to the inlet hose, and
   configured to supply the fresh liquid to the tissue via the inlet hose.

In an application, the apparatus includes a controller pack, the controller pack including a controller, the controller configured to control transmission of electrical power to the pump.

In an application, the controller is configured to receive the power from a battery.

In an application, the controller is configured to receive the power from an external power input.

In an application:
   the blade assembly includes a distal end, a proximal end, and a longitudinal axis therebetween;
   the blade head is disposed at the distal end, and the exhaust hole is disposed laterally to the longitudinal axis, the apparatus being configured to discharge the refuse liquid laterally through the exhaust hole.

In an application, the exhaust hole is disposed proximal from the blade head.

In an application, the blade assembly housing defines a handle proximal from the blade head.

There is further provided, in accordance with an application of the present invention, apparatus for conditioning ex vivo pericardial tissue, the tissue having a parietal side, and a fibrous side from which fibers extend, the apparatus including:
- a blade assembly including:
  - a blade head including:
    - a blade array; and
    - a face, the face defining gaps therein, the gaps dimensioned to facilitate protrusion therethrough of the fibers into the blade head, such that movement of the blade array with respect to the face, shears the fibers that protrude through the gaps into the blade head;
  - a drive shaft;
  - a motor, operatively coupled to the blade array via the drive shaft, so as to be configured to move the blade array relative to the face;
  - a blade-assembly housing that houses the blade head, the motor, and the drive shaft;
- a battery pack; and
- a flexible electrical cord flexibly coupling the battery pack to the blade-assembly housing thereby facilitating movement of the blade assembly in relation to the battery pack, and electrically connecting the battery back to the motor.

In an application, the apparatus includes a battery housed within the battery pack.

In an application, the motor is operatively coupled to the blade array via the drive shaft, so as to be configured to rotate the blade array relative to the face.

In an application, the blade assembly does not include a battery.

In an application, the cord is reversibly connectable to the battery pack.

In an application, the cord is reversibly connectable to the blade assembly.

In an application:
the blade assembly is configured to be used while the tissue is submerged in a liquid, with the fibers facing upward, with the face facing downward, and with the blade array submerged in the liquid;
the blade-assembly housing is shaped to define an exhaust hole; and
the apparatus is configured to generate, while the blade array is submerged in the liquid, a suction force that sucks the liquid into the blade head via the gaps, and discharges a refuse liquid through the exhaust hole.

In an application, the apparatus includes a refuse hose connected to the exhaust hole, and leading away from the blade assembly.

In an application, the apparatus is configured such that movement of the blade array with respect to the face generates the suction force.

In an application, the apparatus is configured such that rotation of the blade array with respect to the face generates the suction force.

In an application, the apparatus includes a pump, the pump being:
fluidly connected to the exhaust hole; and
configured to generate the suction force.

In an application, the apparatus includes a refuse hose connected to the exhaust hole, and the pump is fluidly connected to the exhaust hole via the refuse hose.

In an application, the apparatus includes an inlet hose, the inlet hose configured to be connected to a source of fresh liquid, and the pump is:
connected to the inlet hose, and
configured to supply the fresh liquid to the tissue via the inlet hose.

In an application:
the blade assembly includes a distal end, a proximal end, and a longitudinal axis therebetween;
the blade head is disposed at the distal end, and
the exhaust hole is disposed laterally to the longitudinal axis, the apparatus being configured to discharge the refuse liquid laterally through the exhaust hole.

In an application, the exhaust hole is disposed proximal from the blade bead.

In an application, the blade assembly housing defines a handle proximal from the blade head.

In an application, the battery pack includes a controller, and the controller is configured to control the motor.

In an application, the controller is configured to control transmission of power from the battery to the motor.

In an application, the controller includes a variable resistor.

In an application, the blade assembly includes a controller, and the controller is configured to control the motor.

In an application, the controller is configured to control transmission of power from the battery to the motor.

In an application, the controller includes a variable resistor.

There is further provided, in accordance with an application of the present invention, apparatus for conditioning ex vivo pericardial tissue, the tissue having a parietal side, and a fibrous side from which fibers extend, the apparatus including:
- a blade assembly including:
  - a blade head that includes:
    - a blade array; and
    - a face, the face defining gaps therein, the gaps dimensioned to facilitate protrusion therethrough of the fibers into the blade head, such that movement of the blade array with respect to the face shears the fibers that protrude through the gaps into the blade head;
  - a motor,
  - a drive shaft, the drive shaft operatively connecting the motor to the blade array; and
  - a blade-assembly housing that houses the blade head, the motor, and the drive shaft;
- a controller pack, the controller pack including a controller, the controller configured to control the motor; and
- a flexible electrical cord electrically connecting the controller pack to the blade-assembly housing, thereby facilitating movement of the blade assembly in relation to the controller pack, the controller pack being configured to power, via the cord, the motor to move the blade array relative to the face.

In an application, the controller is configured to power the motor to move the blade array rotationally, relative to the face.

In an application, the apparatus includes a battery, the battery being configured to power the controller pack.

In an application, the battery is co-housed with the controller in the controller pack.

In an application, the controller is configured to control transmission of power from the battery to the motor.

In an application, the controller includes a variable resistor.

In an application, the cord is reversibly connectable to the controller pack.

In an application, the cord is reversibly connectable to the blade assembly.

In an application:
the blade assembly is configured to be used while the tissue is submerged in a liquid, with the fibers facing upward, with the face facing downward, and with the blade array submerged in the liquid;
the blade-assembly housing is shaped to define an exhaust hole; and
the apparatus is configured to generate, while the blade array is submerged in the liquid, a suction force that sucks the liquid into the blade head via the gaps, and discharges a refuse liquid through the exhaust hole.

In an application, the apparatus includes a refuse hose connected to the exhaust hole, and leading away from the blade assembly.

In an application, the apparatus is configured such that movement of the blade array with respect to the face generates the suction force.

In an application, the apparatus is configured such that rotation of the blade array with respect to the face generates the suction force.

In an application, the apparatus includes a pump, the pump being:
fluidly connected to the exhaust hole; and
configured to generate the suction force.

In an application, the apparatus includes a refuse hose connected to the exhaust hole, and the pump is fluidly connected to the exhaust hole via the refuse hose.

In an application, the apparatus includes an inlet hose, the inlet hose configured to be connected to a source of fresh liquid, and the pump is:
connected to the inlet hose, and
configured to supply fresh liquid to the tissue via the inlet hose.

In an application:
the blade assembly includes a distal end, a proximal end, and a longitudinal axis therebetween;
the blade head is disposed at the distal end, and
the exhaust hole is disposed laterally to the longitudinal axis, the apparatus being configured to discharge the refuse liquid laterally through the exhaust hole.

In an application, the exhaust hole is disposed proximal from the blade head.

In an application, the blade assembly housing defines a handle proximal from the blade head.

There is further provided, in accordance with an application of the present invention, a system for conditioning ex vivo pericardial tissue, the tissue having a parietal side, and a fibrous side from which fibers extend, the system including:
a blade assembly including:
a blade head that includes:
a blade array; and
a face, the face defining gaps therein, the gaps dimensioned to facilitate protrusion therethrough of the fibers into the blade head, such that movement of the blade array, with respect to the face, shears the fibers that protrude through the gaps into the blade head;
a motor;
a drive shaft, the drive shaft operatively connecting the motor to the blade array; and
a blade-assembly housing that houses the blade head, the motor, and the drive shaft;
a bath; and
a tissue restraint, configured to secure the tissue within the bath.

In an application, the apparatus includes a support plate, and the tissue restraint is configured to secure the tissue to the support plate, the support plate being configured to support the tissue, and the bath being dimensioned to receive a portion of the support plate.

In an application, the bath has a floor, the floor defining a recess, the recess shaped to receive the portion of the plate.

In an application, the tissue restraint includes at least one bracket

In an application, the bracket and the plate each include holes, the holes of the bracket and the holes of the plate being aligned complementarily.

In an application:
the bath has a floor, the floor defining a recess dimensioned to snugly receive the tissue, and
the tissue restraint is coupled to the bath, and is configured to secure the tissue within the recess.

In an application, the tissue restraint includes at least one bracket.

In an application:
the blade assembly is configured to be used while the tissue is submerged in a liquid with the fibers facing upward, with the face facing downward, and with the blade array submerged in the liquid;
the blade-assembly housing is shaped to define an exhaust hole; and
the blade assembly is configured to generate, while the blade array is submerged in the liquid, a suction force that sucks the liquid into the blade head via the gaps, and discharges a refuse liquid through the exhaust hole.

In an application, the apparatus includes a refuse hose connected to the exhaust hole, and leading away from the blade assembly.

In an application, the apparatus is configured such that movement of the blade array with respect to the face generates the suction force.

In an application, the apparatus is configured such that rotation of the blade array with respect to the face generates the suction force.

In an application, the apparatus includes a pump, the pump being:
fluidly connected to the exhaust hole; and
configured to generate the suction force.

In an application, the apparatus includes a refuse hose connected to the exhaust hole, and the pump is fluidly connected to the exhaust hole via the refuse hose.

In an application, the apparatus includes an inlet hose, the inlet hose configured to be connected to a source of fresh liquid, and the pump is:
connected to the inlet hose, and
configured to supply the fresh liquid to the tissue via the inlet hose.

In an application:
the blade assembly includes a distal end, a proximal end, and a longitudinal axis therebetween;
the blade head is disposed at the distal end, and the exhaust hole is disposed laterally to the longitudinal axis, the apparatus being configured to discharge the refuse liquid laterally through the exhaust hole.

In an application, the exhaust hole is disposed proximal from the blade head.

In an application, the blade assembly housing defines a handle proximal from the blade head.

In an application, the apparatus includes a controller pack, the controller pack including a controller configured to control the motor.

In an application, the controller is configured to control transmission of power from a battery to the motor.

In an application, the controller includes a variable resistor.

In an application, the blade assembly includes a controller, and the controller is configured to control the motor.

In an application, the controller is configured to control transmission of power from a battery to the motor.

In an application, the controller includes a variable resistor.

There is further provided, in accordance with an application of the present invention, a method for conditioning ex vivo pericardial tissue, the tissue having a parietal side, and a fibrous side from which fibers extend, the method including:
providing a blade assembly, the blade assembly including a blade head, the blade head including a blade array and a face, the face defining gaps therein;
placing the parietal side of the tissue downward against a support plate;
operating a motor to move the blade array with respect to the face; and
contacting the face with the tissue such that the fibers protrude through the gaps into the blade head, and the blade array shears the fibers that protrude through the gaps into the blade head, yielding sheared fibers.

In an application, the method includes mechanically securing the tissue to the support plate using a tissue restraint.

In an application, contacting the face with the tissue includes contacting the face with a first portion of the tissue, and the method includes subsequently contacting the face with a second portion of the tissue.

In an application, the method includes:
adding a liquid to a bath,
submerging the tissue in the liquid within the bath, with the fibers facing upward, and
contacting the face with the tissue includes contacting the face with the tissue with the face facing downward.

In an application,
the bath is dimensioned to define a built-in support plate, and
placing the tissue involves placing the tissue against the built-in support plate.

In an application, submerging the face of the blade head in the liquid within the bath.

In an application, the bath has a floor defining a recess dimensioned to snugly receive the plate, and the method includes fitting the plate and the tissue into the recess.

In an application:
the blade-assembly housing defines an exhaust hole,
applying the blade assembly to the tissue includes submerging the face and the blade array in a liquid; and
the method includes generating a suction force that:
sucks the liquid into the blade head via the gaps, and
discharges, through the exhaust hole, a refuse liquid including the liquid and
the sheared fibers.

In an application, discharging the refuse liquid includes flushing the sheared fibers, with the refuse liquid, out from the blade-assembly housing, laterally through the exhaust hole.

In an application, the method includes draining the refuse liquid via a refuse hose.

In an application, generating the suction force includes generating the suction force using a pump, the pump being fluidly connected to the exhaust hole.

In an application, the method includes discarding, using the pump, the refuse liquid via a refuse hose that fluidly connects the pump to the exhaust hole.

In an application, the method includes supplying fresh liquid to the tissue via an inlet hose.

In an application, supplying fresh liquid to the tissue includes supplying, using the pump, the fresh liquid via an inlet hose that fluidly connects the pump to the tissue.

In an application:
the blade-assembly housing defines an exhaust hole,
applying the blade assembly to the tissue includes submerging the face and the blade array in a liquid; and
operating the motor includes operating the motor such that movement of the blade array with respect to the face generates a suction force that:
sucks the liquid into the blade head via the gaps, and
discharges, through the exhaust hole, a refuse liquid including the liquid and
the sheared fibers.

In an application, operating the motor includes operating the motor such that rotation of the blade array with respect to the face generates the suction force.

In an application, operating the motor includes controlling transmission of electrical power to the motor via a controller.

In an application, controlling the transmission of electrical power includes controlling the transmission of electrical power using a controller pack that is flexibly connected to the blade assembly via a flexible cord.

The present invention will be more fully understood from the following detailed description of applications thereof, taken together with the drawings, in which:

DETAILED DESCRIPTION OF EMBODIMENTS

Figure 1:
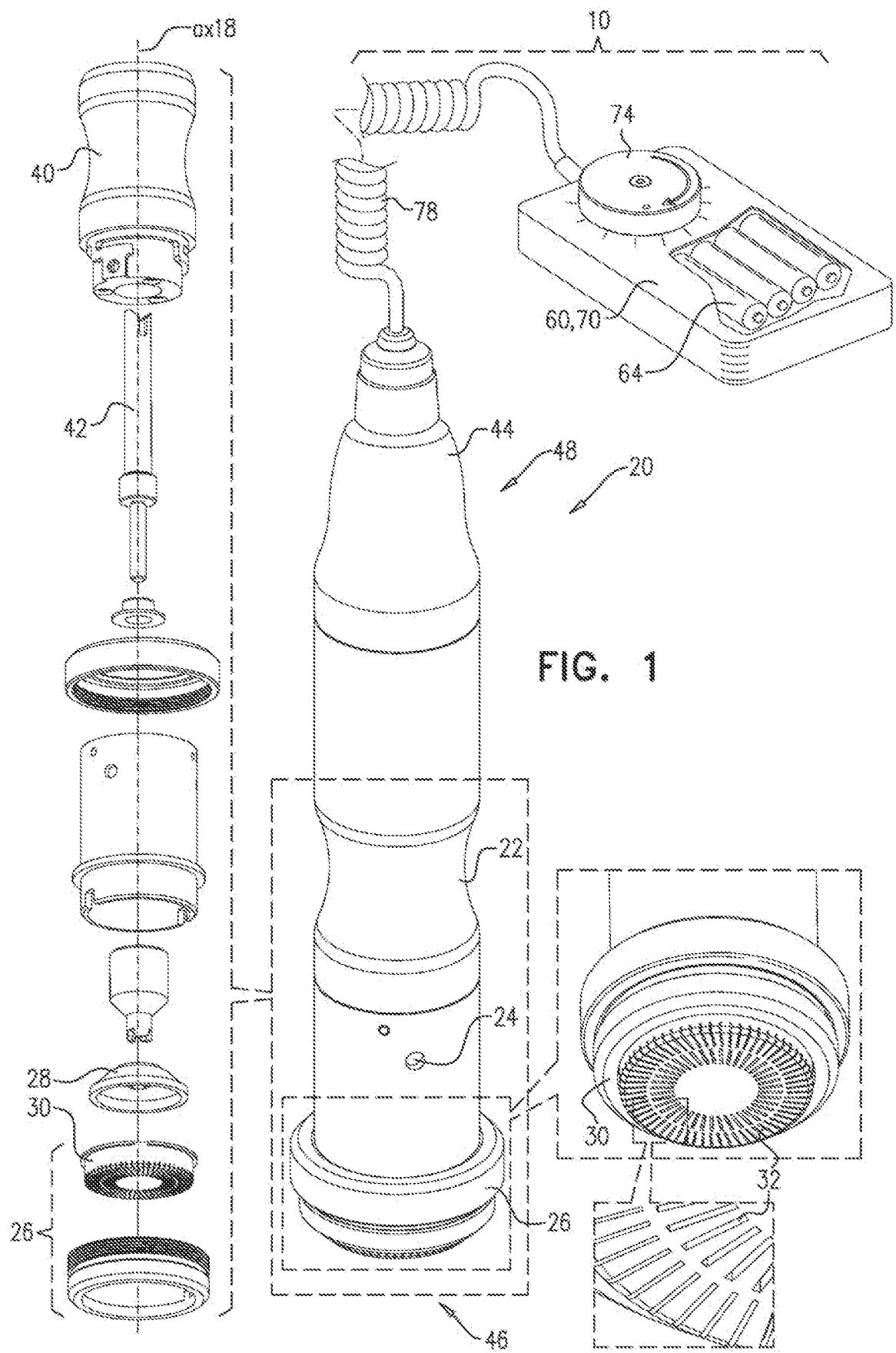
FIG. 1 is a schematic illustration of a device comprising a blade assembly, the blade assembly flexibly connected to a controller pack comprising a battery pack and a contoller, in accordance with some applications of the present, invention.
Figure 2:
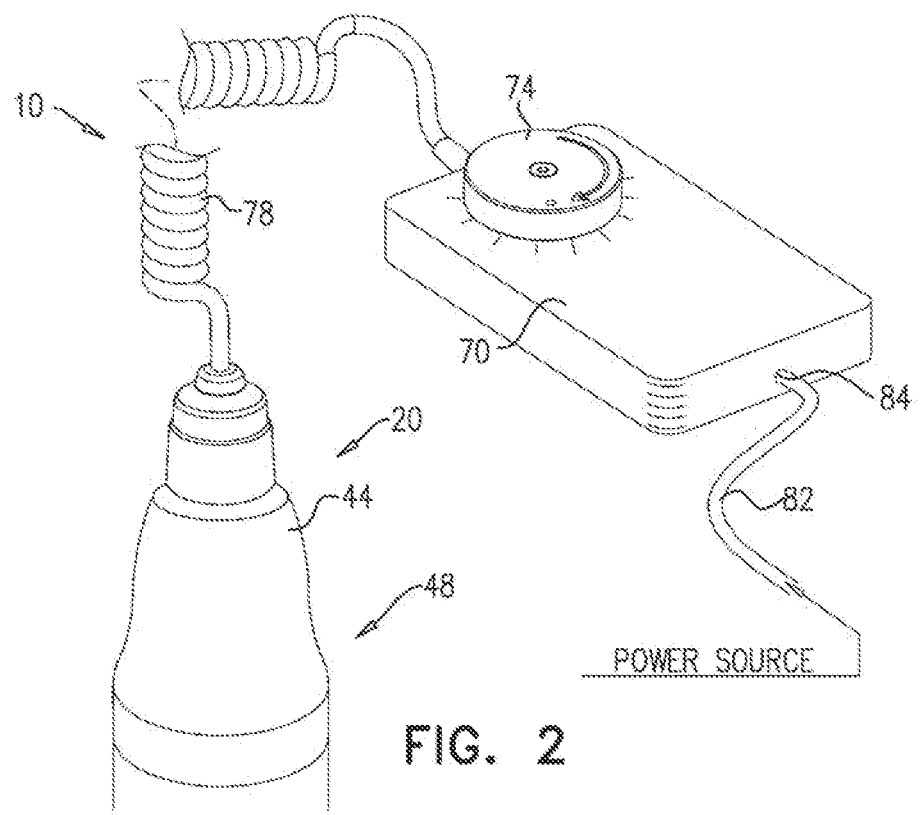
FIG. 2 is a schematic illustration of a device comprising a blade assembly, the blade assembly flexibly connected to a controller pack comprising a controller, in accordance with some applications of the present invention.
Figure 3:
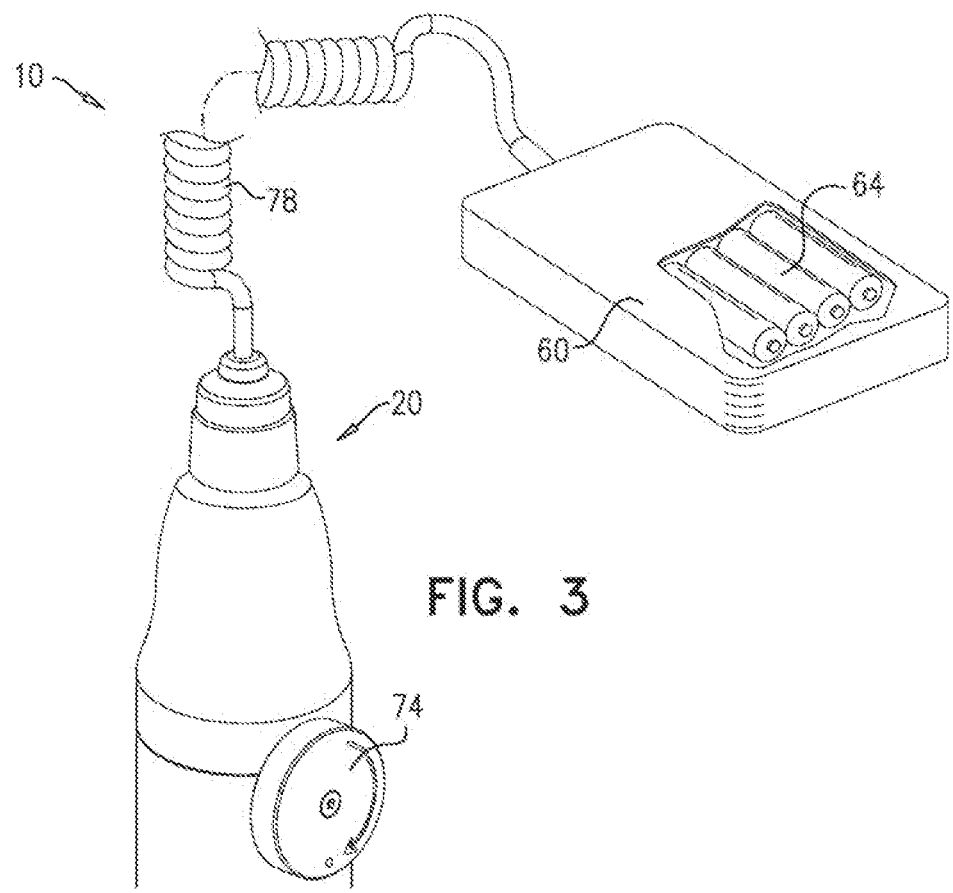
FIG. 3 is a schematic illustration of a device comprising a blade assembly, the blade assembly comprising a controller, and flexibly connected to a battery pack, in accordance with some applications of the present invention.

Reference is made to FIGS. 1-3, which are schematic illustrations of a device 10 for conditioning ex vivo pericardial tissue 110, in accordance with some applications of the invention. In particular, device 10 is used for removing fibers from the fibrous side of the pericardium. This may be performed in order to prepare the tissue for subsequent incorporation, as a prosthetic leaflet, into a prosthetic heart valve.

Typically, and as shown, device 10 comprises a blade assembly 20 having a longitudinal axis ax18, that comprises a blade head 26 on a distal end 46 of the blade assembly, and a handle 44 at a proximal portion 48 of the blade assembly. Blade assembly 20 typically comprises a blade-assembly housing 22 that houses the other components of the blade assembly. Blade assembly 20 is typically hand-held, e.g., having a length of 5-20 cm, a maximum width of 1-10 cm, and/or a weight of 0.05-1 kg (e.g., 50-500 g, such as 50-200 g). For some applications, blade assembly 20 (e.g., housing 22) is configured (e.g., dimensioned and/or shaped) to be held like a pen, e.g., to facilitate finely controlled movement of the blade assembly by the user. Blade head 26 comprises a face 30, which defines gaps 32, which are dimensioned to facilitate protrusion therethrough of the fibers into blade head 26. A blade array 28 is disposed within blade head 26, adjacent to and proximal of face 30. Blade array 28 is operatively connected to a motor 40 via a drive shaft 42. Typically, and as shown, drive shaft 42 is disposed along longitudinal axis ax18. When in operation, motor 40 moves (e.g. rotates) blade array 28, relative to face 30, shearing fibers that protrude through gaps 32 into blade head 26.

For some applications, and as shown in FIGS. 1 and 3, device 10 comprises a battery pack 60 that houses, or is configured to house, a battery 64. For some applications, and as shown, battery 64 may comprise one or more commercially-available batteries, typically supplied by the user. For other applications, battery pack 60 comprises battery 64, which may or may not be integral to battery pack 60. For such applications, battery 64 is typically rechargeable.

For such applications, battery pack 60 is flexibly connected to blade assembly 20 by a flexible electrical cord 78, the flexibility of the cord facilitating movement of the blade assembly in relation to the battery pack. Battery 64 powers motor 40 via cord 78. That is, cord 78 electrically connects battery 64 to motor 40. For some applications, cord 78 is reversibly connectable to battery pack 60, and/or to blade assembly 20. Typically, and as shown, blade assembly 20 does not comprise a battery.

Typically, and as shown in FIGS. 1, 2, and 3, device 10 comprises a controller 74.

Controller 74 controls motor 40, e.g., by controlling electrical power that is transmitted to the motor. For some applications, controller 74 comprises a variable resistor, although other means for regulating electrical power are also contemplated. For some applications, controller 74 is a switch, e.g., having discrete states, such as an on/off switch, or a switch that provides discrete motor speeds.

Typically, controller 74 comprises a control dial, knob or switch. Although the FIGS. 1, 2, and 3 referred to herein depict controller 74 as comprising a dial serving as a user interface, this depiction is not intended to exclude other possible user interfaces, be they mechanical (e.g. buttons or levers), electronic (e.g., touchscreen) or other.

For some applications, e.g., as shown in FIGS. 1 and 2, controller 74 is housed by a controller pack 70, e.g., flexibly coupled and electrically connected to blade assembly 20 via cord 78. In some applications, adjusting controller 74 variably regulates electrical power that is transmitted from controller pack 70, via flexible electrical cord 78, to motor 40 of blade assembly 20. For example, and as shown in FIG. 1, controller 74 may be co-housed with battery 64, e.g., such that battery pack 60 also serves as a controller pack 70.

Alternatively, and as shown in FIG. 2, controller pack 70, comprising controller 74, may be provided independently of a battery pack. Similarly to as described above in reference to battery pack 60, flexible connection of controller pack 70 to blade assembly 20 via flexible cord 78 facilitates movement of the blade assembly in relation to the controller pack. In the embodiment shown in FIG. 2, controller 74 powers motor 40 via cord 78. That is, cord 78 electrically connects controller 74 to motor 40. For some applications, cord 78 is reversibly connectable to contoller pack 70, and/or to blade assembly 20.

For some applications, and as shown in FIG. 2, battery pack 60 is absent. Typically, for applications lacking battery pack 60, and as shown, an external power cord 82 supplies electrical power, at a power input 84 of controller pack 70.

For other applications, as illustrated in FIG. 3, blade assembly 20 comprises controller 74. For such applications, controller 74 typically receives electrical power, via cord 78, from battery pack 60. For some applications, adjusting controller 74 typically variably regulates electrical power that is transmitted to motor 40 of blade assembly 20.

Figure 4A:
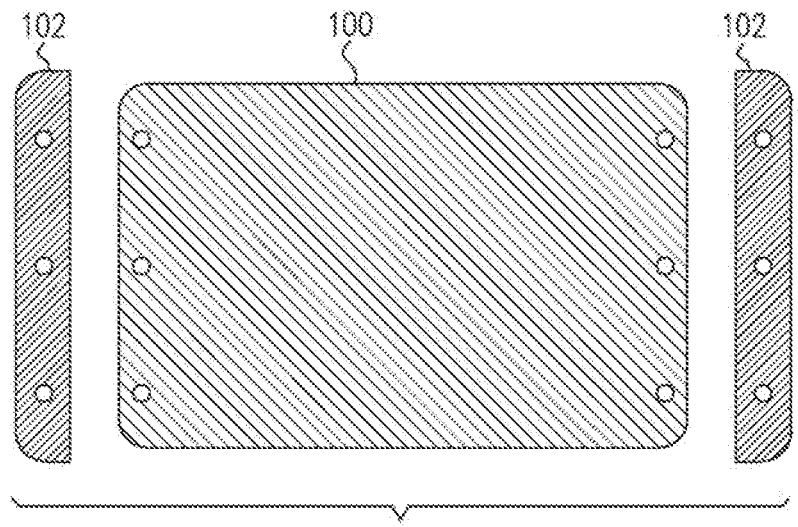
FIGS. 4A-C are schematic illustrations of a support plate and a tissue restraint for inserting ex vivo pericardial tissue into a bath, in accordance with some applications of the present invention.
Figure 4B:
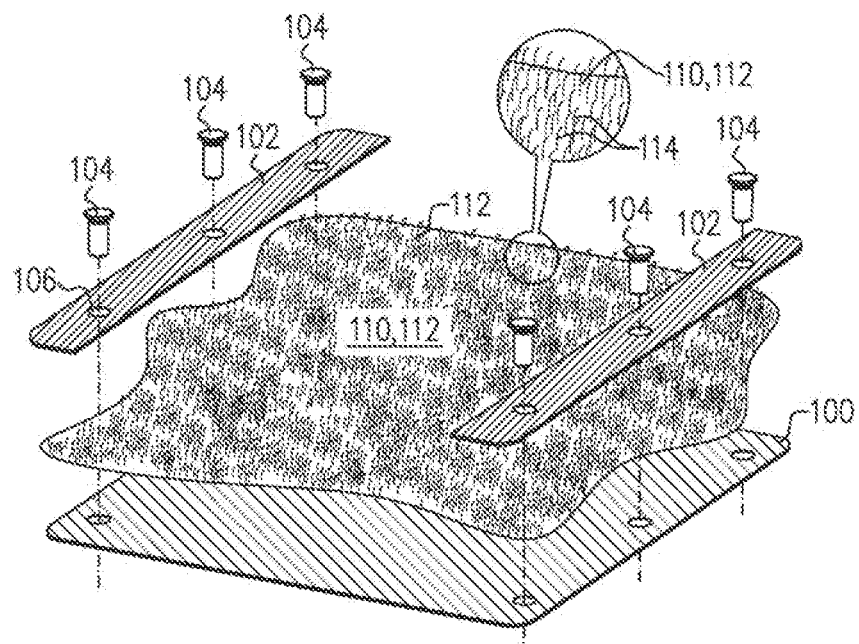
Figure 4C:
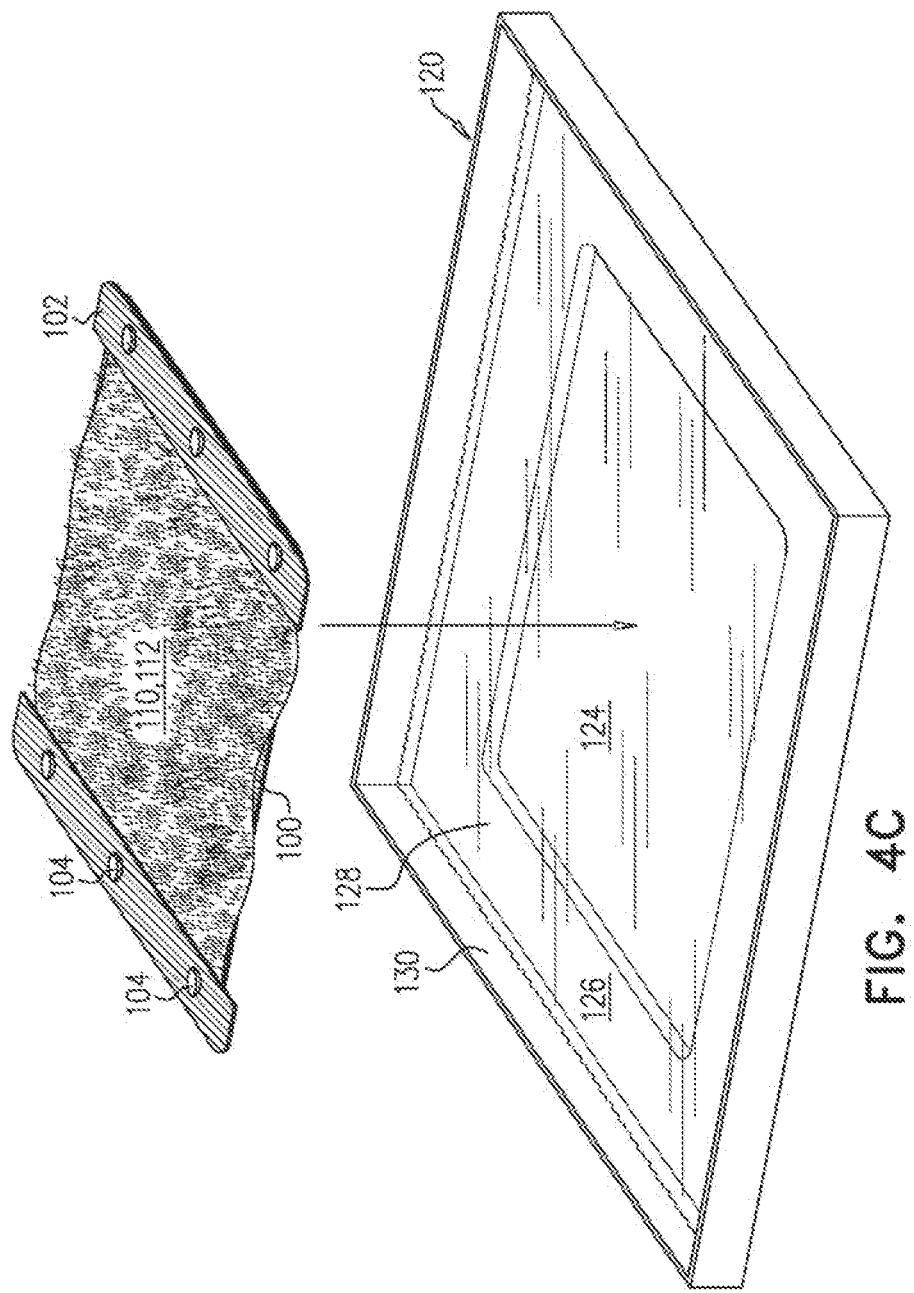

Reference is made to FIGS. 4A-C, which are schematic illustrations of a support plate 100 and a tissue restraint 102 being used to submerge ex vivo pericardial tissue 110 in a liquid 126 within a bath 120, in accordance with some applications of the invention.

For some applications, and as shown, ex vivo pericardial tissue 110 is placed against support plate 100, and is mechanically secured to the support plate by attaching a tissue restraint 102 to the plate. Typically, and as shown, a parietal side of tissue 110 is placed downward against plate 100, exposing a fibrous side 112 of the tissue, from which fibers 114 extend upwards.

For some applications, and as shown in FIG. 4C, tissue 110, secured to plate 100, is placed into a bath 120. Typically, bath 120 is dimensioned to facilitate submerging tissue 110 in a liquid 126 within the bath. For some applications, and as shown, bath 120 is dimensioned to define a recess 124 in a floor 128 of the bath. Typically, plate 100, tissue restraint 102 and tissue 110 are fitted into recess 124 by the user.

For some applications, and as shown, tissue restraint 102 comprises at least one bracket, configured to secure the tissue to the plate. As shown, for such applications the support plate and the brackets typically comprise holes 106 aligned complementarily to facilitate mechanical fastening of the brackets to the plate (e.g. by screws 104). However, it is to be noted that the scope of the invention includes other mechanisms for securing tissue 110 to plate 100, such as clamps.

As shown in FIG. 4C, recess 124 is dimensioned to snugly receive plate 100. In other applications (not shown), recess 124 is dimensioned to define a built-in support plate configured to snugly receive tissue 110, and the tissue is affixed to the built-in support plate. In such applications, tissue restraint 102 is typically coupled to bath 120.

Figure 5A:
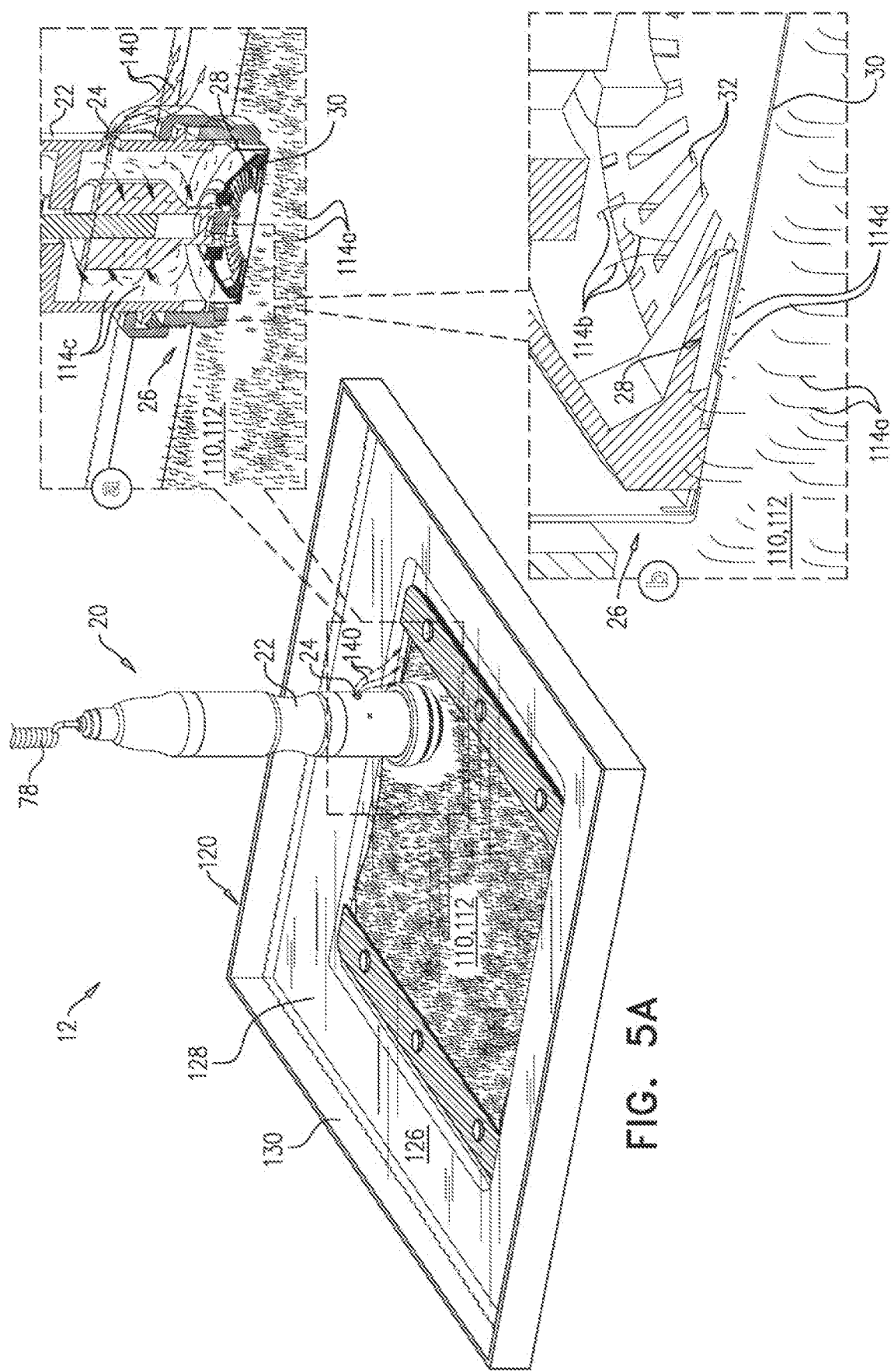
FIGS. 5A-B are schematic illustrations of ex vivo pericardial tissue secured to a support plate, the plate and tissue submerged in a liquid within a bath for removal of fibers from the tissue by applying an electrically powered blade assembly to the tissue, in accordance with some applications of the present invention.
Figure 5B:
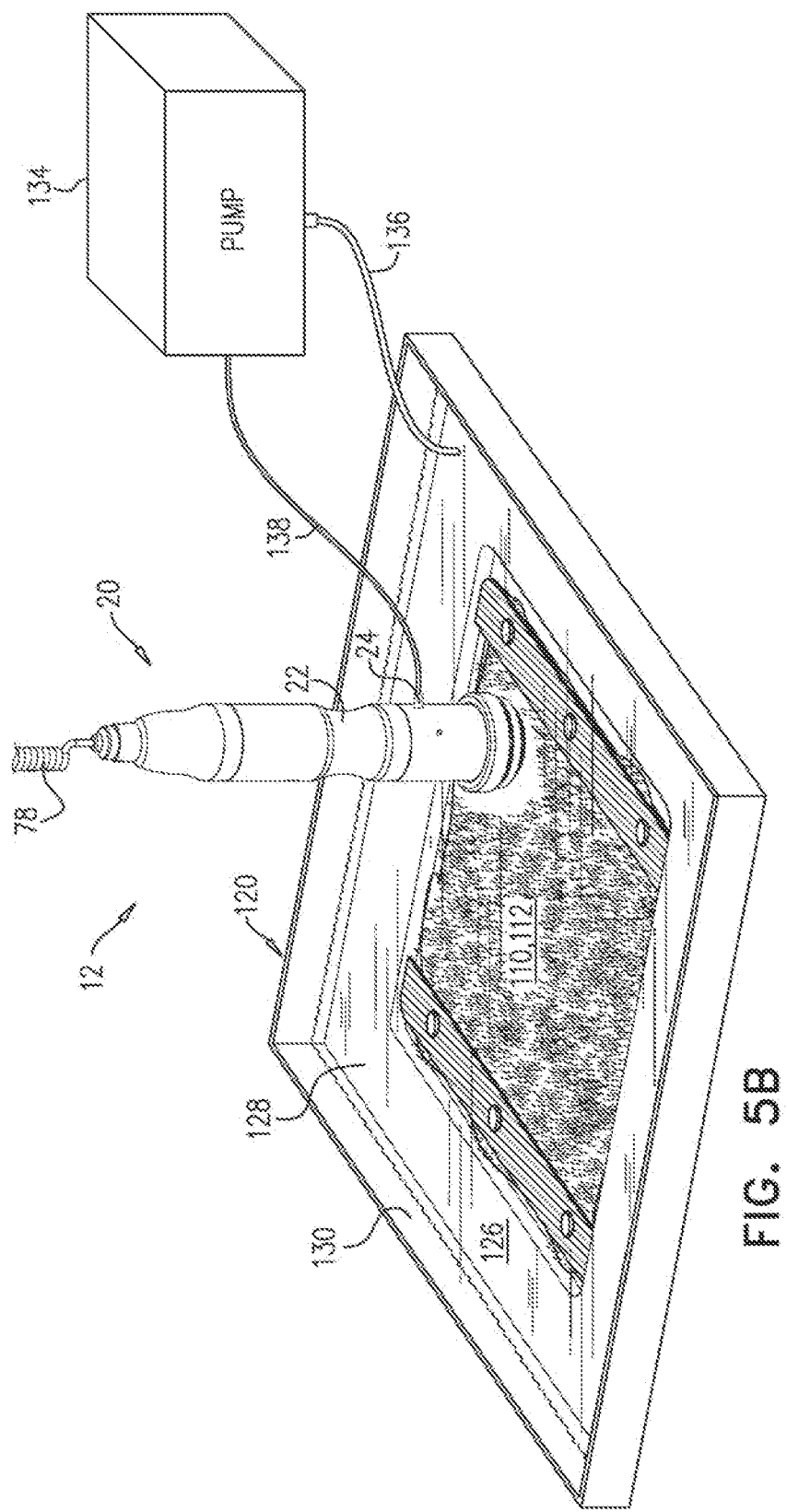

Reference is made to FIGS. 5A-B, which are schematic illustrations showing shearing of fibers 114 from tissue 110 using blade assembly 20, in accordance with some applications of the invention. Typically, and as shown, this is performed while the tissue is submerged in liquid 126 within bath 120.

Typically, and as shown in FIG. 5A, bath 120 comprises side-walls 130 extending upward from floor 128, facilitating submerging tissue 110 in liquid 126 within bath 120. Typically, and as shown, tissue 110 is submerged in liquid 126 with fibrous side 112 (and therefore fibers 114) facing upward.

Typically, face 30 of blade head 26 on distal end 46 of blade assembly 20 is applied downward upon fibrous side 112 of tissue 110, such that upward-extending fibers 114 protrude through gaps 32 into blade head 26. In inset "b" of FIG. 5A, reference numeral 114a indicates fibers that have not yet been contacted by assembly 20, and reference numeral 114b indicates fibers that protrude through gaps 32 in face 30, prior to shearing. As described hereinabove, motor 40 moves (e.g., rotates) blade array 28, relative to face 30, so as to shear fibers 114b. Reference numeral 114c indicates sheared ends 114c of the fibers, and reference numeral 114d indicates the residual base or rot of the fibers that may remain after shearing.

Typically, blade assembly 20 is moved over tissue 110, in order to shear fibers disposed at various portions of the tissue. That is, face 30 is contacted with a first portion of tissue 110 in order to shear the fibers at the first portion, and is then contacted with a second portion of the tissue, and so on. This may be achieved by lifting face 30 away from the tissue before placing it in contact with the second portion of the tissue, or by sliding the face across the tissue, e.g., while it remains in contact with the tissue.

Typically, and as shown in inset "a" of FIG. 5A, sheared ends 114c are released within blade head 26 after shearing of fibers 114. For some applications, it is desirable to flush sheared fibers 114c that might otherwise accumulate within blade head 26. For such applications, sheared fibers 114c are flushed, with refuse a liquid 140, out from blade-assembly housing 22 through exhaust hole 24. Typically, a suction force flushes sheared fibers 114c from blade head 26. Further typically, and as shown, face 30 and blade array 28 are submerged in liquid 126, and blade-assembly housing 22 is shaped to define exhaust hole 24. Typically, and as shown, exhaust hole 24 is a lateral exhaust hole, disposed laterally to longitudinal axis ax18 (e.g, in a lateral wall of blade-assembly housing 22). For such applications, operation of blade assembly 20 generates a suction force which sucks liquid 126 into blade head 26 through gaps 32 in face 30, and discharges refuse liquid 140 via exhaust hole 24, e.g., laterally from the blade assembly. Typically, therefore, liquid 126 is sucked in from a distal end of blade assembly 20, and is discharged laterally from the blade assembly.

While liquid 126 is sucked through blade head 26 to exhaust hole 24, the liquid dislodges sheared fibers 114c from blade array 28, flushing the sheared fibers with the liquid, out from blade-assembly housing 22 through the exhaust hole. The use of the suction force to flush sheared fibers 114c from blade head 26 via exhaust hole 24 is hypothesized by the inventors to reduce the need for a separate blade-cleaning procedure, making the use of blade assembly 20 more time-efficient.

Typically, and as shown in inset "a" of FIG. 5A, bath 120 is filled with liquid 126 to a depth such that the liquid covers face 30 of blade head 26, but does not cover exhaust hole 24, when the face is applied to tissue 110. In this way, face 30 is typically submerged in liquid 126, whereas exhaust hole 24 is typically not submerged in liquid 126, during operation of blade assembly 20. For some applications, exhaust hole 24 is at least 1 cm (e.g., 1-10 cm, such as 1-5 cm) above face 30. It is hypothesized by the inventors that submerging face 30 in liquid 126 facilitates flushing of sheared fibers 114c from blade array 28 by sucking the liquid and sheared fibers 114c into blade head 26. It is further hypothesized by the inventors that not submerging exhaust hole 24 facilitates discharging the liquid via exhaust hole 24, by less impeding discharge of refuse liquid 140 through the exhaust hole, compared to if the exhaust hole were submerged.

For some applications, while blade array 28 is submerged in liquid 126, the movement of the blade array by motor 40 generates the suction force that sucks the liquid into blade head 26 via gaps 32, dislodges sheared fibers 114c from blade array 28 and discharges the refuse liquid 140 via exhaust hole 24. For such applications, the movement of the blade array that generates the suction force is typically rotational movement.

For some applications, e.g., as shown in FIG. 5A, refuse liquid 140 is discharged via exhaust hole 24 into bath 120.

For some applications, e.g., as shown in FIG. 5B, a pump 134 generates the suction force. For some applications, and as shown, pump 134 is connected to a refuse hose 138 configured to drain refuse liquid 140 through exhaust hole 24, away from blade assembly 20.

Although refuse hose 138 is shown as part of an embodiment including pump 134, the refuse hose may be used independently of the pump. For example, the suction force may be generated without a pump (e.g., by movement of blade array 28, as described hereinabove, mutatis mutandis), and refuse liquid 140 may be discharged via hose 138.

For some applications, and as shown, pump 134 is connected to an inlet hose 136 configured to supply fresh liquid 126 to bath 120, e.g., at the same rate at which refuse liquid 140 is discharged.

For some applications, inlet hose 136 is configured to supply fresh liquid 126 to tissue 110 independently of pump 134 (e.g., by being gravity-fed from a source of fresh liquid 126).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that am not in the prior art, which would occur to persons skilled in the art upon reading the foregoing description.

The invention claimed is:

1. A method for conditioning ex vivo pericardial tissue, the tissue having a parietal side, and a fibrous side from which fibers extend, the method comprising:
   providing a blade assembly, the blade assembly including a blade head, the blade head including a blade array and a face, the face defining gaps therein;
   placing the parietal side of the tissue downward against a support plate;
   operating a motor to move the blade array with respect to the face; and
   contacting the face with the tissue such that the fibers protrude through the gaps into the blade head, and the blade array shears the fibers that protrude through the gaps into the blade head, yielding sheared fibers.

2. The method according to claim 1, wherein the method further comprises mechanically securing the tissue to the support plate using a tissue restraint.

3. The method according to claim 1, wherein contacting the face with the tissue comprises contacting the face with a first portion of the tissue, and wherein the method further comprises, subsequently contacting the face with a second portion of the tissue.

4. The method according to claim 1, wherein the method further comprises:
adding a liquid to a bath,
submerging the tissue in the liquid within the bath, with the fibers facing upward, and
contacting the face with the tissue comprises contacting the face with the tissue with the face facing downward.

5. The method according to claim 4, wherein:
the bath is dimensioned such that the support plate is a built-in support plate, and
placing the tissue comprises placing the tissue against the built-in support plate.

6. The method according to claim 4, further comprising submerging the face of the blade head in the liquid within the bath.

7. The method according to claim 4, wherein the bath has a floor defining a recess dimensioned to receive the support plate, the method further involving fitting the support plate and the tissue into the recess.

8. The method according to claim 1, wherein:
the blade assembly further comprises a blade assembly housing shaped to define an exhaust hole,
contacting the face with the tissue comprises submerging the face and the blade array in a liquid; and
the method further comprises generating a suction force that:
sucks the liquid into the blade head via the gaps, and
discharges, through the exhaust hole, a refuse liquid comprising the liquid and the sheared fibers.

9. The method according to claim 8, wherein discharging the refuse liquid comprises flushing the sheared fibers, with the refuse liquid, out from the blade assembly housing, laterally through the exhaust hole.

10. The method according to claim 9, wherein the method further comprises draining the refuse liquid via a refuse hose.

11. The method according to claim 1, wherein:
the blade assembly further comprises a blade assembly housing shaped to define an exhaust hole,
contacting the face with the tissue comprises submerging the face and the blade array in a liquid, and
operating the motor comprises operating the motor such that movement of the blade array with respect to the face generates a suction force that:
sucks the liquid into the blade head via the gaps, and
discharges, through the exhaust hole, a refuse liquid comprising the liquid and the sheared fibers.

12. The method according to claim 11, wherein operating the motor comprises operating the motor such that rotation of the blade array with respect to the face generates the suction force.

13. The method according to claim 1, wherein operating the motor comprises controlling transmission of electrical power to the motor via a controller.

14. The method according to claim 13, wherein controlling the transmission of electrical power comprises controlling the transmission of electrical power using a controller pack that is flexibly connected to the blade assembly via a flexible cord.

* * * * *